(12) United States Patent
Levatich

(10) Patent No.: US 8,870,887 B2
(45) Date of Patent: Oct. 28, 2014

(54) SEALING HOLES IN BONY CRANIAL ANATOMY USING CUSTOM FABRICATED INSERTS

(76) Inventor: Mark Levatich, Brooktondale, NY (US)

( * ) Notice: Subject to any disclaimer, the term of this patent is extended or adjusted under 35 U.S.C. 154(b) by 857 days.

(21) Appl. No.: 12/903,324

(22) Filed: Oct. 13, 2010

(65) Prior Publication Data

US 2011/0087232 A1    Apr. 14, 2011

Related U.S. Application Data

(60) Provisional application No. 61/251,036, filed on Oct. 13, 2009.

(51) Int. Cl.
| | |
|---|---|
| *A61B 17/60* | (2006.01) |
| *A61F 2/00* | (2006.01) |
| *A61B 17/88* | (2006.01) |
| *A61F 2/28* | (2006.01) |
| *A61B 17/84* | (2006.01) |

(52) U.S. Cl.
CPC ............ *A61F 2/2875* (2013.01); *A61B 17/842* (2013.01); *A61B 17/8861* (2013.01); *A61B 17/8822* (2013.01); *A61B 17/8811* (2013.01); *A61B 17/8872* (2013.01)
USPC .......................................................... 606/94

(58) Field of Classification Search
USPC ..................... 606/92–94, 86 R; 623/16.11, 623/17.11–17.16
See application file for complete search history.

(56) References Cited

U.S. PATENT DOCUMENTS

| | | | | |
|---|---|---|---|---|
| 7,682,364 B2* | 3/2010 | Reiley et al. | ..................... | 606/93 |
| 7,909,873 B2* | 3/2011 | Tan-Malecki et al. | ..... | 623/17.11 |
| 8,147,500 B2* | 4/2012 | Beyar et al. | ..................... | 606/94 |
| 8,282,648 B2* | 10/2012 | Tekulve | .......................... | 606/92 |
| 2007/0270841 A1 | 11/2007 | Badie | | |
| 2009/0264892 A1 | 10/2009 | Beyar et al. | | |

OTHER PUBLICATIONS

Cappabianca et al. "Sellar Repair in Endoscopic Endonasal Transsphenoidal Surgery: Results of 170 Cases." Neurosurgery, vol. 51, No. 6, pp. 1365-1372. Dec. 2002.

* cited by examiner

*Primary Examiner* — Anu Ramana
(74) *Attorney, Agent, or Firm* — Brown & Michaels, PC

(57) ABSTRACT

An apparatus and method to implant a seal in a skull base defect. The seal is implanted using apparatus with deployable elements which pass up the nasal cavity into the area of the sphenoid sinus where they deploy and expand into useful conformations. A disk is inserted through the skull base defect into an interior side of the skull at the base defect, with a stalk extending through the skull base defect. The stalk is held outward from the skull base defect, holding the disk against the interior side of the skull while a conical mold is filled with bone cement. Once the cement has cured, the apparatus is removed, leaving the insert in the skull with the stalk surrounded by a cone of bone cement, creating a water tight seal in said skull base defect.

10 Claims, 24 Drawing Sheets

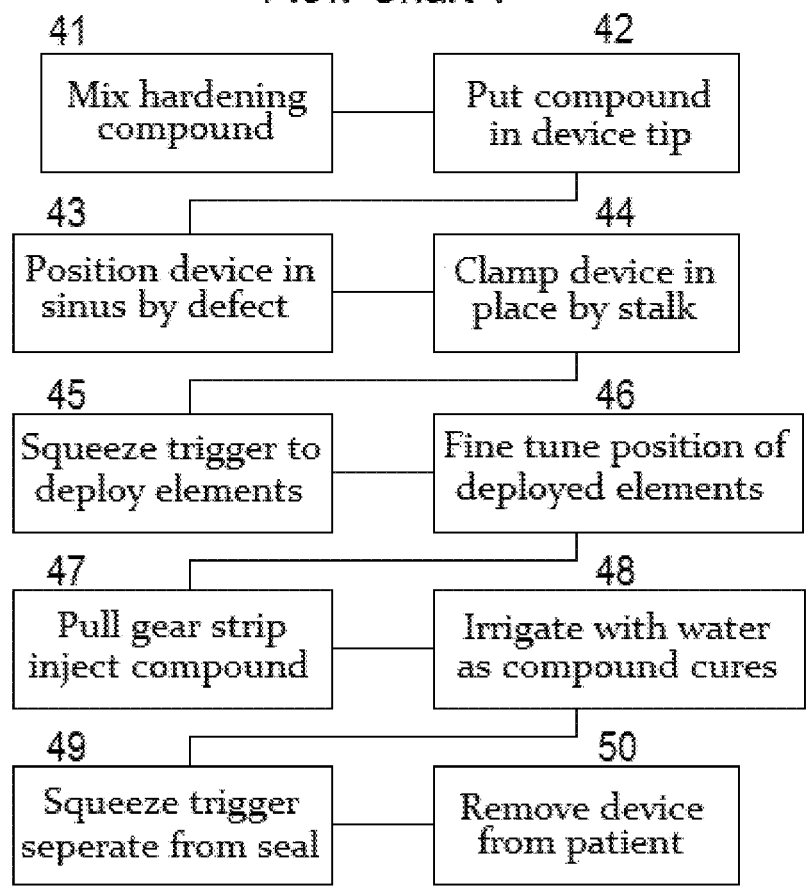

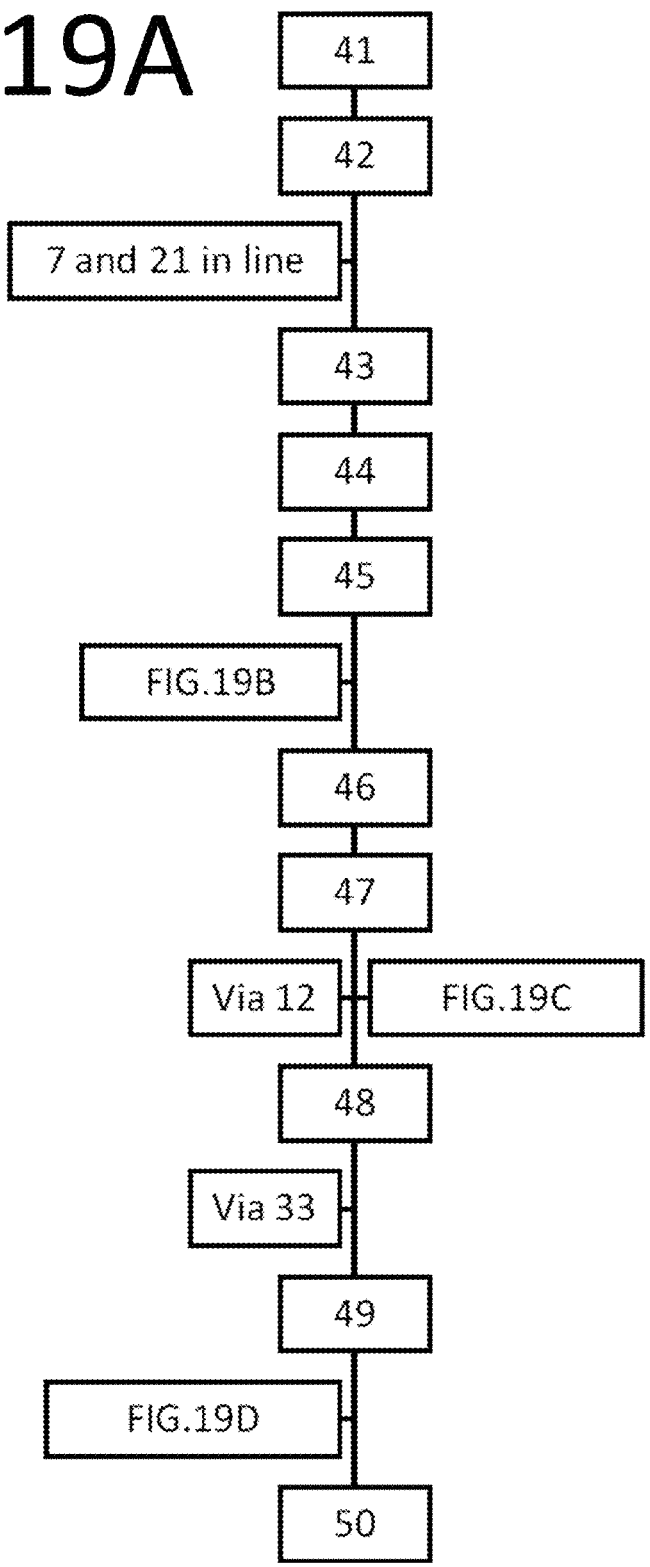

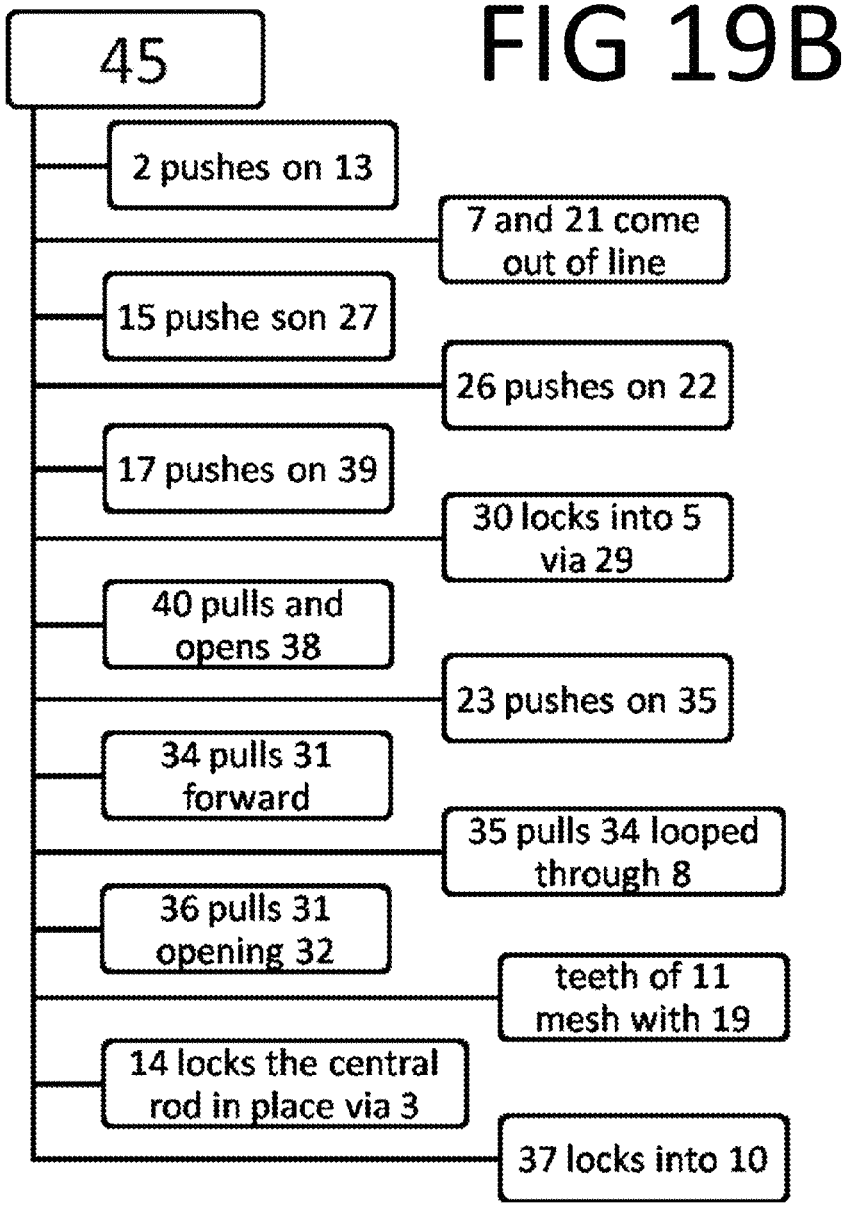

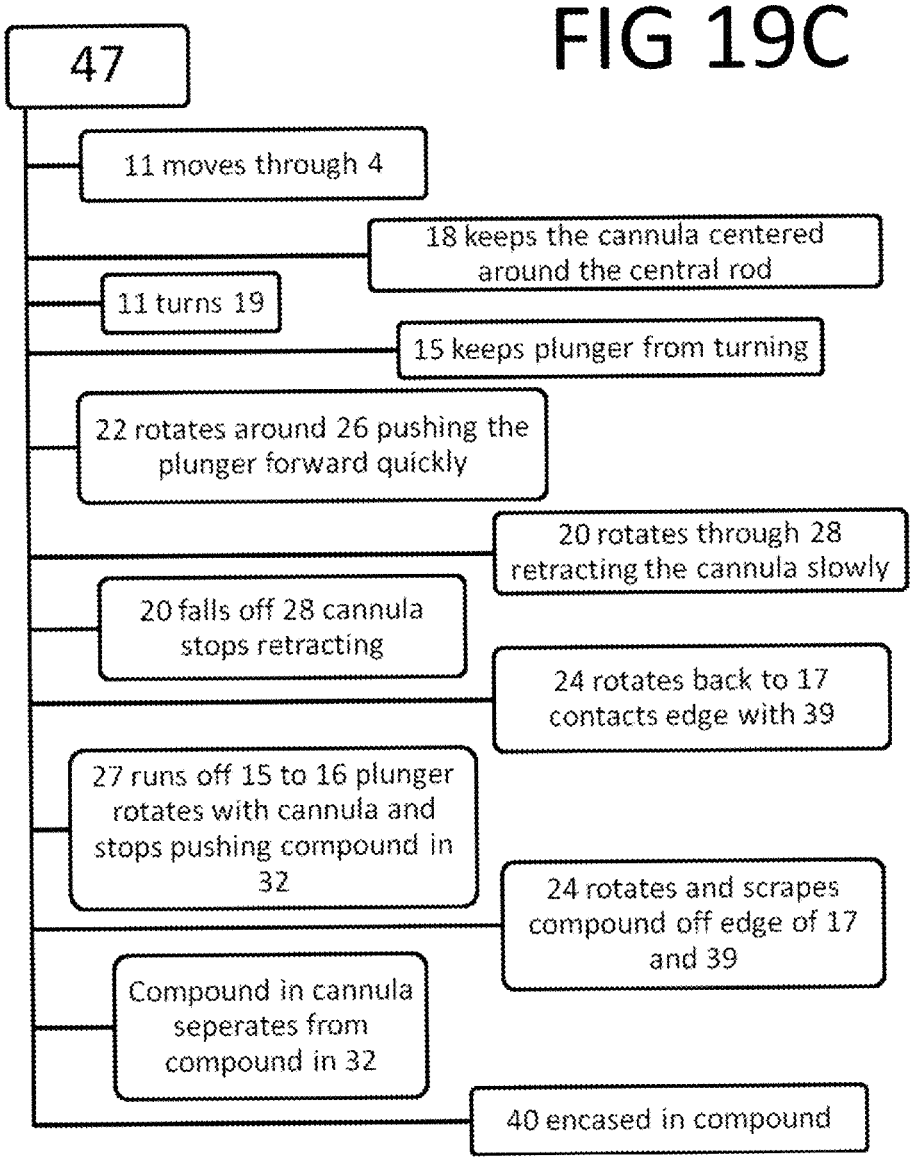

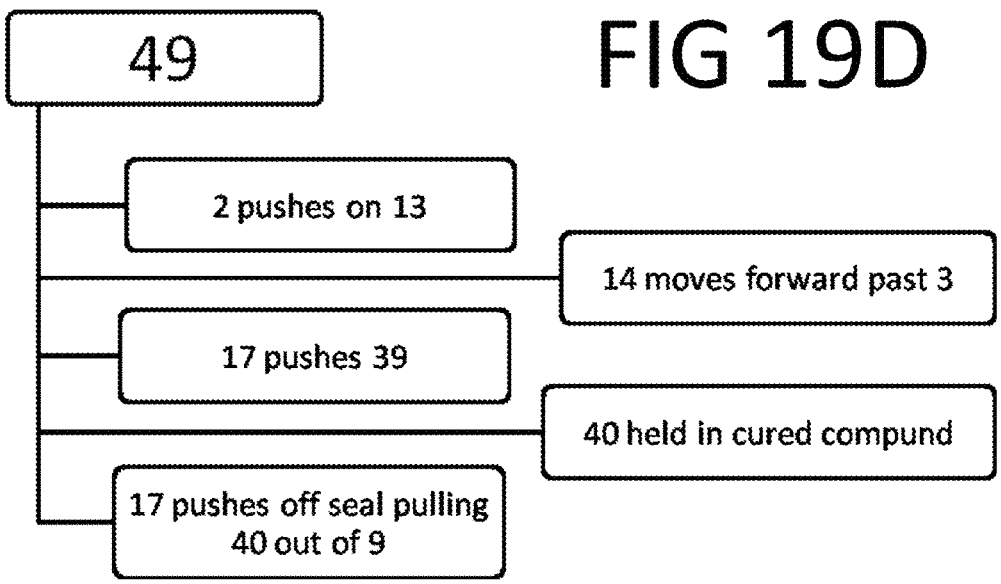

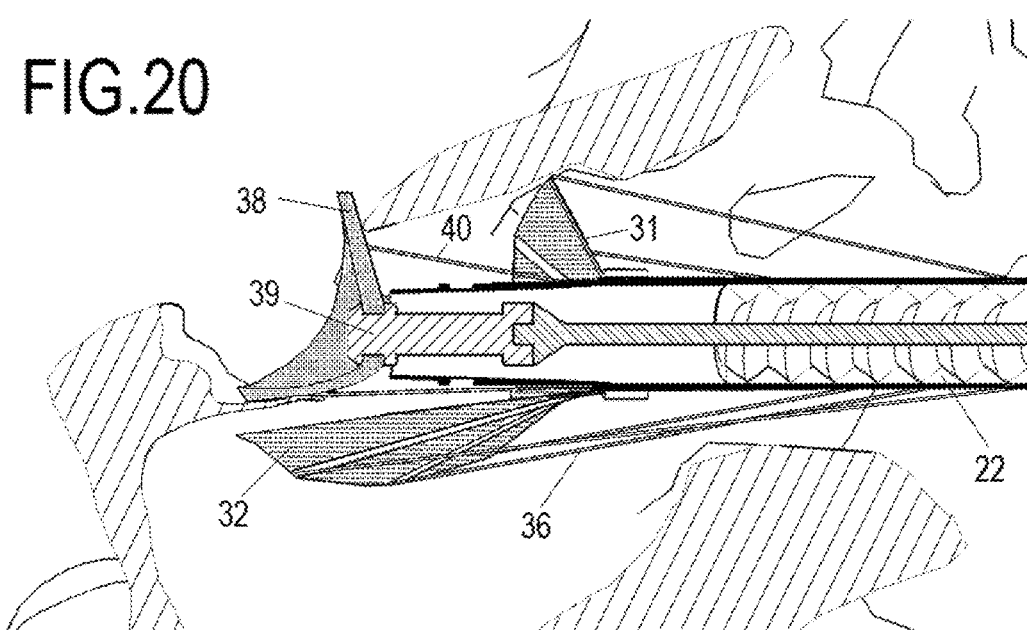

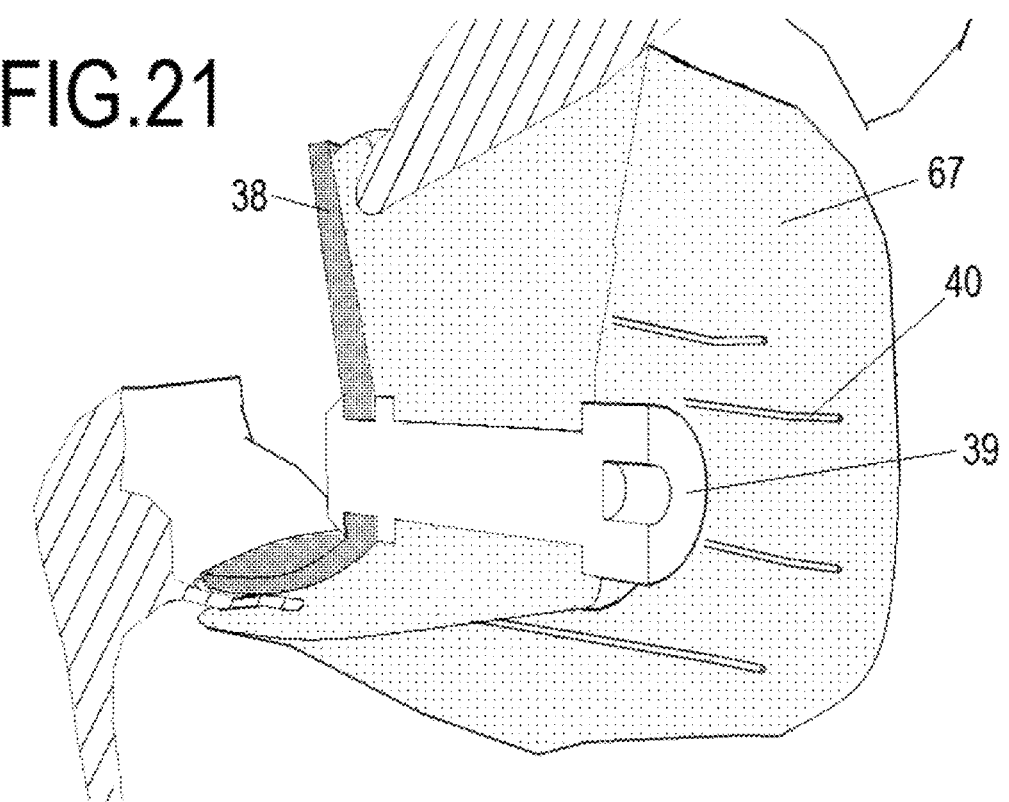

US 8,870,887 B2

SEALING HOLES IN BONY CRANIAL ANATOMY USING CUSTOM FABRICATED INSERTS

REFERENCE TO RELATED APPLICATIONS

This application claims an invention which was disclosed in Provisional Application No. 61/251,036, filed 13 Oct. 2009, entitled "SEALING HOLES IN BONY ANATOMY USING TISSUE REPLACEMENT & BONE CEMENT". The benefit under 35 USC §119(e) of the United States provisional application is hereby claimed, and the aforementioned application is hereby incorporated herein by reference.

FIELD OF THE INVENTION

The invention pertains to the field of surgical instruments. More particularly, the invention pertains to surgical instruments for reconstruction in endonasal neurosurgery.

BACKGROUND OF THE INVENTION

One of the existing procedures to remove brain tumors at the skull base is endonasal neurosurgery. This surgery uses the nose and sinuses as a pathway to access the base of the skull. Instruments are used to erode away bone to create a hole in the back of the sinuses through the sphenoid sinus and in proximity to the sella turcica; this area is referred to as the skull base. A skull base defect is any opening in the bony layer, filled with tissue or not, between the brain cavity and any of the sinuses. This surgery is done primarily to remove tumors on or near the pituitary gland. However there are cases where the patient has preexisting holes in the bone between the brain cavity and the sinuses. In general this embodiment is used to seal all holes between the sinuses and brain cavity regardless of the manner in which the hole is made. The most common manner and thus the most thoroughly discussed are holes made by surgeons for removal of tumors.

The most difficult stage of endonasal neurosurgery is closing the hole in the skull. The current method of sealing a hole in the skull base involves inserting fat, often harvested from the patient's belly button, in to the hole. This is followed by packing multiple pieces of biocompatible foam into the hole and sealing it with glue; often fibrin glue.

Endonasal neurosurgery has a mortality rate of less than 1% but a morbidity rate of 12%. The majority of morbidity (9%) is the result of skull base seals failing. It is important to note that the traditional closing procedure makes a plug to mend the tissue layer but does nothing to replace the bone that is removed to enter the skull. The patient has a permanent hole in their skull which contributes to long term morbidity. Complications include but not limited to cerebral spinal fluid leakage and meningitis.

US Published Patent Application 2007/0270841 presents an implantable device for sealing the sphenoid sinus or sella turcica. This publication does not describe any use of a compounded that sets to a hardened state to seal a defect. This publication does not describe a device to assist in the placement of a seal. This publication does not describe a seal made of a plurality of materials.

"Sellar Repair in Endoscopic Endonasal Transsphenoidal Surgery: Results of 170 Cases", published in *Neurosurgery* 51:1365-1372 by Cappabianca et. al. in 2002 describes the most common method used by those skilled in the art for sealing a skull base defects. This publication does not describe the use of a compound that sets to a hardened state to seal a defect. This publication does not describe a device other than commonly available surgical tools for tissue resection and manipulation to assist in the placement of a seal.

SUMMARY OF THE INVENTION

The present invention provides an apparatus and method to implant a seal in a skull base defect with a compound that is initially a viscous fluid and hardens to provide a solid water tight seal to the hole. The seal is implanted using apparatus with deployable elements that are compact so that they may pass up the nasal cavity into the area of the sphenoid sinus where there is room for them to deploy and expand into useful conformations. A disk is inserted through the skull base defect into an interior side of the skull at the skull base defect, with a stalk extending through the skull base defect. The stalk is held outward from the skull base defect, holding the disk against the interior side of the skull while a conical mold is filled with a material that sets to a hardened state. An example of such material is bone cement Once the cement has cured, the apparatus is removed, leaving the insert in the skull with the stalk surrounded by a cone of bone cement, creating a water tight seal in said skull base defect.

BRIEF DESCRIPTION OF THE DRAWING

FIG. 18 shows the steps taken by the user to use the first embodiment.

FIG. 19A reiterates the steps outlined in FIG. 18 but highlights interactions of the elements that make up the embodiment.

FIGS. 19B-19D are blocks of interactions that occur simultaneously between the user steps.

FIG. 20 shows a cross section of the first embodiment with mold and insert deployed.

FIG. 21 shows a cross section of the final skull base seal.

DETAILED DESCRIPTION OF THE INVENTION

Figure 1:
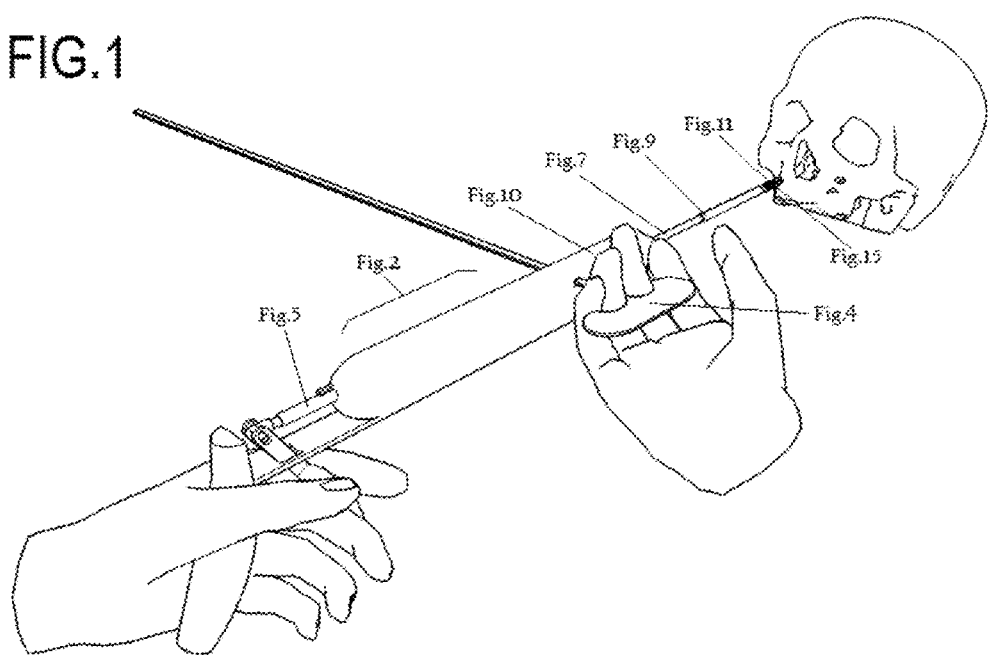
FIG. 1 shows a first embodiment of the invention held by a user with a skull in view.

The invention deploys a prefabricated insert to seal a skull base defect. The first element of the insert is a disk of a flexible material. The disk can be made of harvested tissue, dural graft substitutes, or other flexible biocompatible materials.

The flexible material is attached to a central stalk which is pushed by the embodiment to deploy the insert. The central stalk can be made of cured compound so that the stalk will chemically bond to the compound injected or it can be made of another biocompatible compound and held in place when encased in compound to make the seal.

The insert deploys from being compact within the tip of the embodiment with a series of constraint strings. The strings pass from the flexible disk material to the tip of the embodiment. Pushing of the stalk forward at the center of the graft material and the constraints pulling the edges in the opposite direction forces the graft material to flower open.

The desired placement of the flexible disk of the deployed insert is on the interior (brain side) of the skull base defect. The flexible disk has three purposes; to act as a physical barrier to prevent excess compound from entering the brain cavity, to act as a thermal barrier to prevent thermal ablation of tissue as the compound cures, and depending on the specific material used for the graft, act as a scaffold for cell growth, healing, and resorption of the graft. Resorption of the disk may or may not be important and should not limit the choice of material for the flexible disk. It will be understood that while the term "disk" is used here for the flexible part of the insert which is placed on the interior side of the defect, that the term is not meant to limit the shape of the disk to circular, but other shapes are possible within the teachings of the invention, such as polygons or irregular shapes to custom-fit a given defect.

The second deployable element is for a mold to contain the uncured bone cement. The mold to encase the bone cement is originally on the outside of the embodiment housing and expands with the use of constraint strings like the insert. The embodiment pushes or pulls a ring connected to rigid members. Between the members is a flexible elastic material that can stretch and expand as the rigid members are lifted away from the housing. The members are lifted away from the housing when the ring moves forward and constraint strings attached to the tips of the rigid members prevent them from moving forward. Thus the members lift away from the housing and the elastic material of the mold expands and a roughly conical barrier is pressed up against the back of sinuses to create an isolated space around the defect to receive the sealing compound and prevent its unintended movement in the liquid phase to other parts of the sinus cavity. It is important to note that the constraint strings of the insert are within the mold.

Once the compound has been injected into the mold the constraint strings of the insert are encased in compound. When the compound solidifies the flexible disk is held in place by the constraint strings that are now encased in compound.

The constraint strings of the insert are held in the tip of the embodiment in grooves similar to needles with pop off stitches. With moderate force the strings will pull out of the tip of the embodiment. Prior to compound curing enough force could not be put on the strings to pull them out. Now that the strings are encased in compound the central rod member that pushed the stalk to deploy the insert, can be pushed again to force the embodiment off of the seal and pull the insert constraint strings out of the tip in the process.

Depending on the range of viscosities the compound is expected to have during the handling time of the embodiment, several methods of injecting the compound have been developed and described in detail by the figures and detailed description below. The general structure of the embodiments is described here.

The first embodiment has eight elements with sub-portions, which are shown in the various figures and explained in detail below. The central rod (see FIG. 5) runs down the center of the embodiment. Over the central rod slides the plunger (see FIG. 9). On the tip of the central rod sits the insert (see FIG. 14) which is the element left in the patient when sealing a defect. Over the central rod and plunger comes the rotating cannula (see FIGS. 7-8). The push threads of the rotating cannula mesh with the threads of the plunger. Over the rotating cannula attach the dynamic threads (see FIG. 10). The thread plate of the dynamic threads meshes with the back-threads of the rotating cannula. The rotating cannula and dynamic threads go inside the embodiment housing. Specifically the dynamic threads go into the grooves of the back-thread housing (see FIG. 3). The central rod at the center of this assembly passes out the back of the housing and is attached to the housing trigger (see FIG. 2). Over the tip of the housing is placed the mold (see FIG. 12). The pull strings of the mold are threaded through the deployment holes in the housing and are attached to the cusp ring which rests in a groove on the tip of the rotating cannula. The constraint strings of the mold are embedded in the outside of the housing and the constraint strings of the insert are inserted into the thread grooves at the tip of the housing. The gear strip (see FIG. 4) is inserted into the gear strip hole just prior to use.

The second embodiment has five elements and sub-portions. A central rod of different structure from the first embodiment runs down the center of the second embodiment (see FIG. 24). On the tip of the central rod sits the insert. The insert is off the same structure as the first embodiment. The central rod runs down the center of a static cannula which is attached to a syringe style plunger attached on the outside of the housing (see FIG. 22). At the tip of the housing is a deployable mold of similar construction to that described in the first embodiment. However the mold in this embodiment is pushed forward by the user via a suction apparatus that passes along the outside of the housing.

As shown in FIG. 18 there are several steps performed in series by the user of the first embodiment. During several stages there are a multitude of simultaneous interactions that occur within the embodiment. These interactions are laid out in flow chart two shown in FIG. 19.

As shown in FIG. 18 the first step in using the device (41) is to mix the hardening compound. A wide array of compounds may be used with this embodiment, the critical elements being that the compound is initially in a fluid state and hardens to a solid state and the second being that the compound has been formulated for use with repairing bone.

As shown in FIG. 18 once the compound has been mixed it must be inserted into the embodiment (42). In its initial state the trigger (2) of the embodiment has not been compressed nor has the gear stick been pulled. In this configuration the compound hole (7) of the housing is in line with the compound hole (21) of the rotating cannula. This allows compound to be injected into the compound push threads (22) of the embodiment.

As shown in FIG. 18 once the compound has been prepared and inserted into the embodiment, the embodiment should be positioned in the patient's sinus via the nasal cavity. This should be conducted with the aid of an endoscope to view the surgical site.

As shown in FIG. 18 after the embodiment is in the sinuses it should be clamped using an endoscope vice which is a piece of equipment commonly available in properly furnished operating suites. The clamp site (6) of the housing is narrow specifically so that it is within dimensions to use already available endoscopic positioning equipment available in an operating room. At this point the gear strip should be inserted through the gear strip hole (4) of the housing. Once the trigger of the embodiment has been pulled the gear strip will not be able to be inserted and pulling the trigger cannot be reversed.

Figure 2:
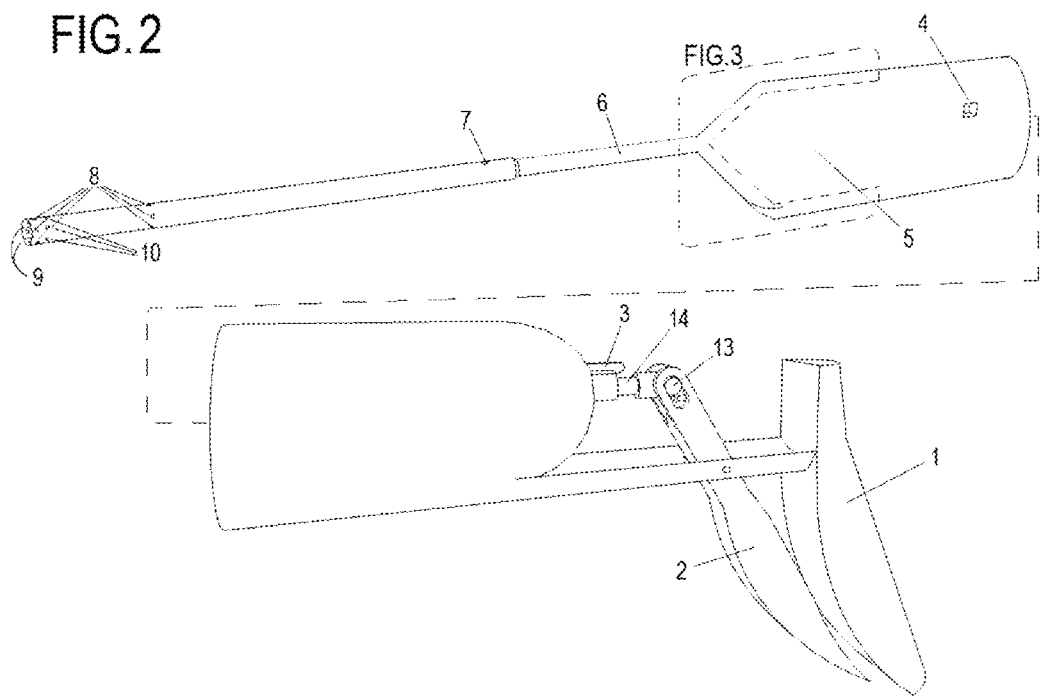
FIG. 2 shows the housing and the sub-portions of this element of the first embodiment.

As shown in FIG. 18 the next step of the user should be to squeeze the trigger (2) of the embodiment. As shown in FIG. 2, the housing of the first embodiment has multiple labeled sub-portions with individual functions. The handle (1) is where the user holds the embodiment to squeeze the trigger (2). When squeezed, the trigger rotates and pushes the trigger bar (13) which pushes the central rod forward. When the central rod moves forward it locks in place when the position flange (3) drops in the position groove (14). The gear strip hole (4) is where the gear strip passes through the housing so that it can engage the rotating cannula gear (19).

Figure 5:
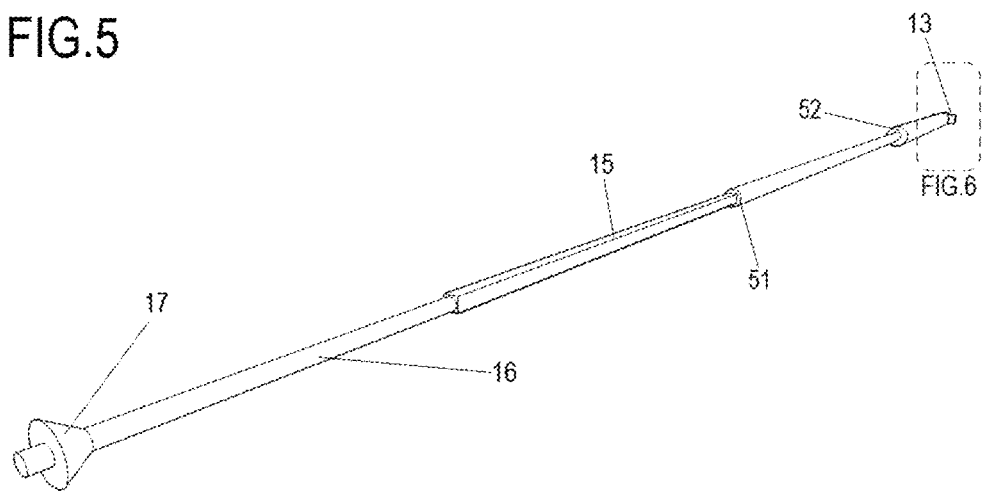
FIG. 5 shows the central rod and the sub-portions of this element of the first embodiment.
Figure 6:
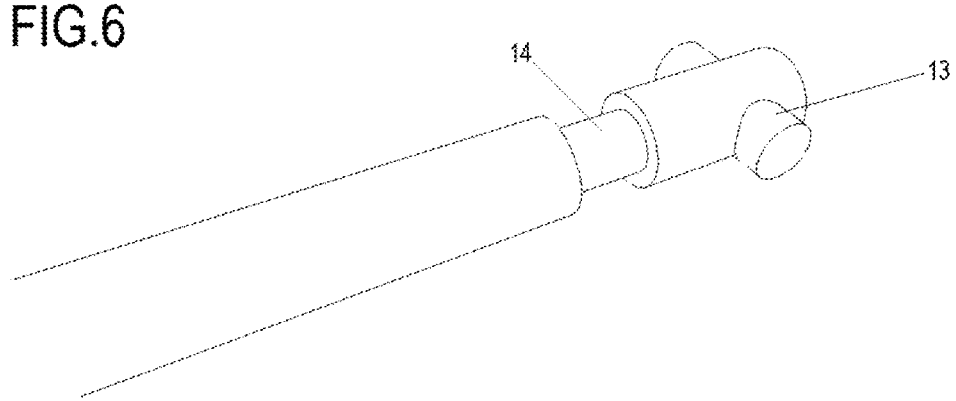
FIG. 6 shows a close up view of trigger bar and position groove.
Figure 17:
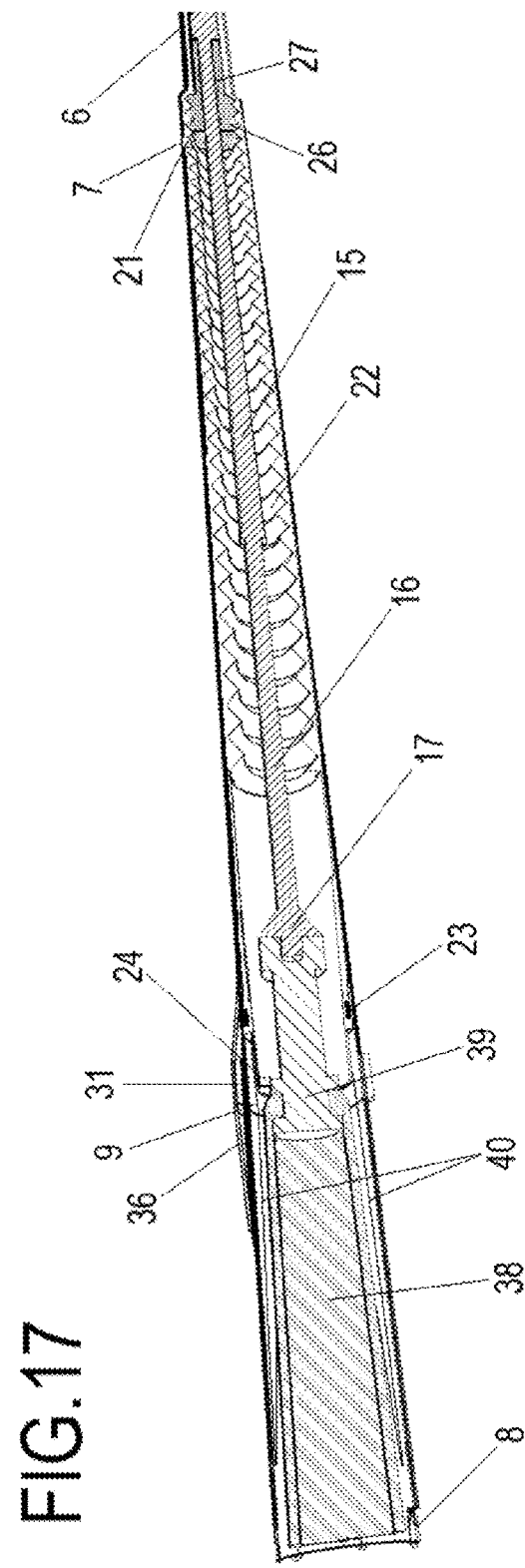
FIG. 17 shows a cross section of the assembled device.

As shown in FIG. 5 the central rod of the first embodiment has several sub-portions. At the tip of the central rod is the bonding protector (17). The bonding protector has a flared tip with a cylindrical extension that fits inside the end of the insert stalk (39). As shown in FIG. 17 the stalk of the insert fits onto the tip of the central rod and the bonding protector covers the end of the stalk. When the central rod moves forward it pushes the stalk forward, which pushes the entire insert out of the tip of the embodiment.

Figure 15A:
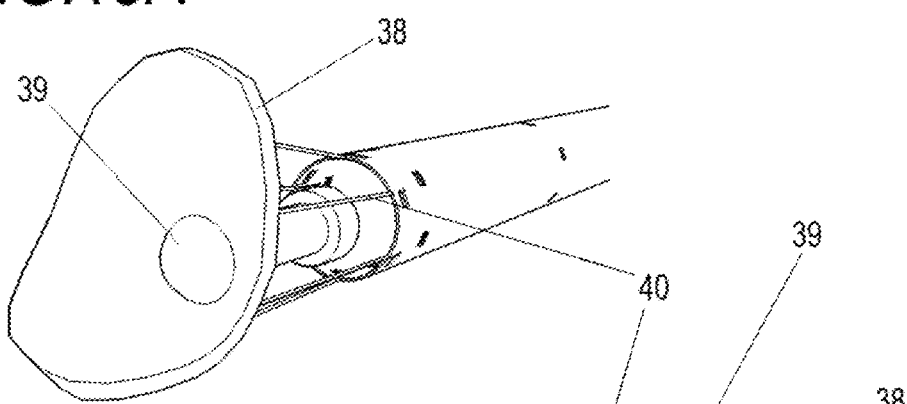
FIG. 15A shows the insert deployed and connected to the tip of the embodiment from a forward profile view.
Figure 15B:
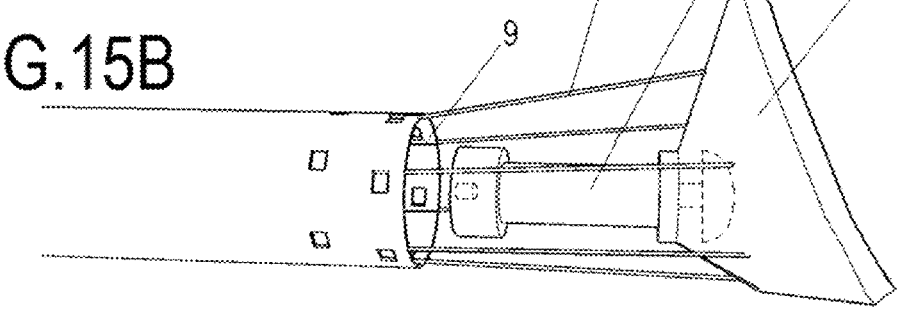
FIG. 15B shows a side view of the insert deployed and connected to the tip of the first embodiment.

As shown in FIGS. 15A and 15B the insert has three sub-portions; the stalk (39), the flexible disk material (38), and the constraint strings (40). The flexible disk material (38) can be made of many biocompatible materials. Its purpose is to act as a scaffold for cell growth and healing, a physical barrier to prevent excess compound from entering the brain cavity, and to act as a thermal barrier so that there isn't thermal damage to tissue as the compound cures. The flexible disk material (38) is attached to the stalk (39) which has a narrower portion on which the flexible disk material is sandwiched by the stalk. Like the flexible disk material there are many materials that could be used for the stalk. This material can either be the same material as the compound so that after the compound cures there is a single homogenous seal or of another material. At the end of the stalk there is a section with greater diameter so that the stalk can be physically contained securely within a cured compound.

Figure 14:
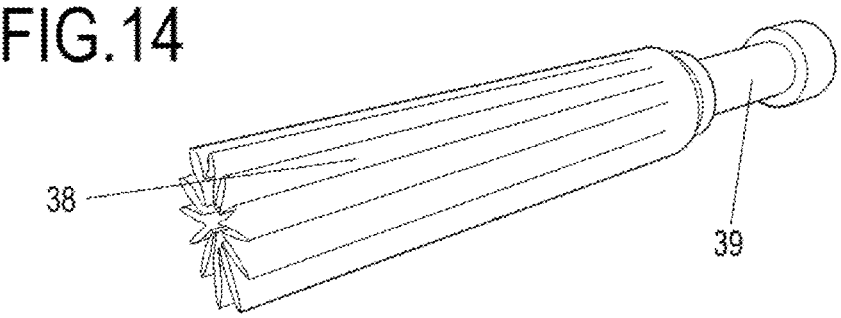
FIG. 14 shows the insert and the sub-portions of the first embodiment.

As shown in FIG. 14 and FIG. 17 before the insert is deployed it is folded up, inside the tip of the housing. When the stalk is pushed forward the insert leaves the end of the housing. After leaving the tip, the constraint strings become taught. Constraint strings (40) attach the flexible disk material (38) to the housing thread grooves (9). When the central rod pushes the stalk, the opposing force on the stalk pushing at the center of the graft material is countered by the strings holding the graft material at points away from the center. The result is the graft material flowers open. Before and after deployment figures can be compared by FIG. 14 and FIG. 15A-15B respectively. The resistance of the flexible disk material (38) to opening is not great enough to pull the constraint stings (40) out of the housing thread grooves (9). Later it will be important that with enough force the insert constraint strings (40) can be pulled from the grooves (9). With correct positioning of the embodiment, the insert can flower open into the skull base defect with the graft material on the brain side of the hole. In addition to pushing the insert the central rod also pushes the plunger.

As shown in FIG. 5 the central rod of the first embodiment has several sub-portions. The squared guide (15) is to guide the plunger and prevent rotation when the cannula rotates with the pulling of the gear strip (47). At the end of the squared guide, the central rod goes from a square cross section to round (51). As shown in FIG. 17 the plunger is initially on the squared guide in contact with face 51. When the central rod moves forward it pushes on the plunger with face 51. As shown in FIG. 17 the plunger is threaded with the compound push threads (22) of the rotating canulla. Thus when the central rod pushes the plunger forward it also pushes the rotating canulla forward.

The rotating cannula moves in several ways, each occurring at different stage of its use. It translates forward when the trigger is pulled. When the gear stick is pulled the cannula is turned by its gear (19) and rotates counter-clockwise when looking at the tip. FIG. 7C shows the back-threads (20) which are threaded so that as the cannula rotates, it also retracts back towards the handle slowly. Midway through pulling the gear strip the back-threads will completely back off the dynamic threads. When the back-threads are no longer threaded with the dynamic threads, the cannula will stop moving backwards but rotation will continue. The central rod guide (18) keeps the rotating cannula sandwiched between the dynamic threads and face 52 of the central rod. Thus there isn't unintended movement of the cannula once it is off of the dynamic threads.

Figure 7A:
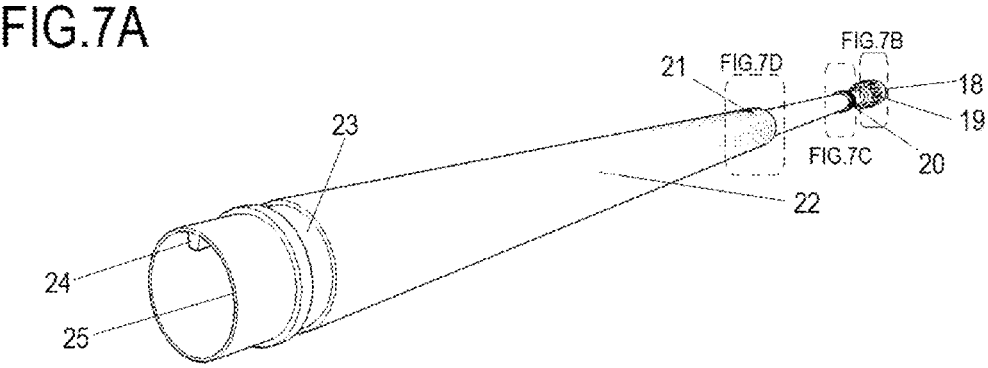
FIG. 7A shows the rotating cannula and the sub-portions of the first embodiment.

FIG. 7A shows the rotating cannula of the first embodiment and the labeled sub-portions of the rotating cannula. The deployment cusp (23) holds a free floating cusp ring (35) so that the rotating cannula can pull the pull strings (34) to deploy the mold when the cannula moves forward. Since the cusp contains a free floating ring (35) the cannula will still be able to rotate later when the gear stick is pulled.

Figure 11A:
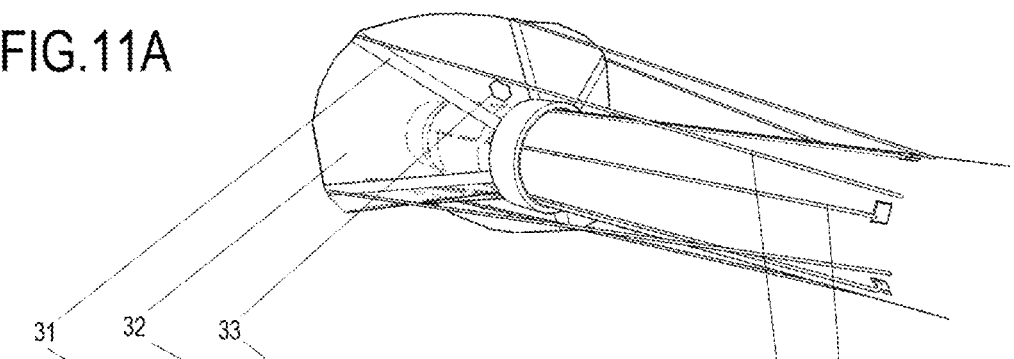
FIG. 11A shows the mold on the tip of the embodiment from a rear profile view and the sub-portions of the first embodiment.
Figure 11B:
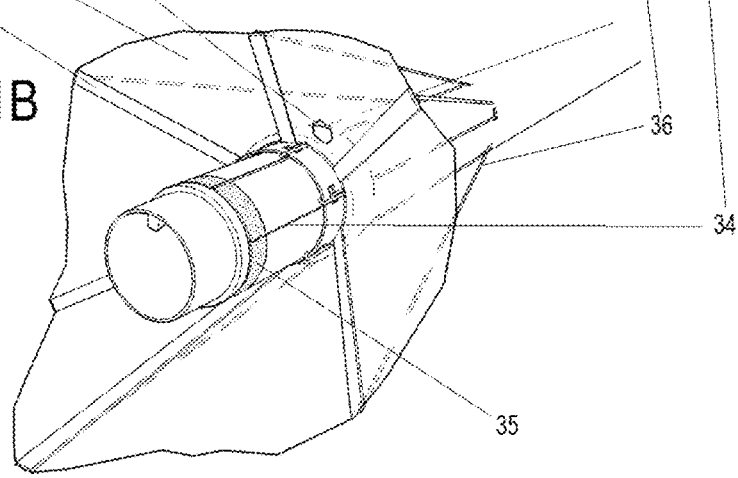
FIG. 11B shows the mold in its open deployed position from a forward profile view.
Figure 12:
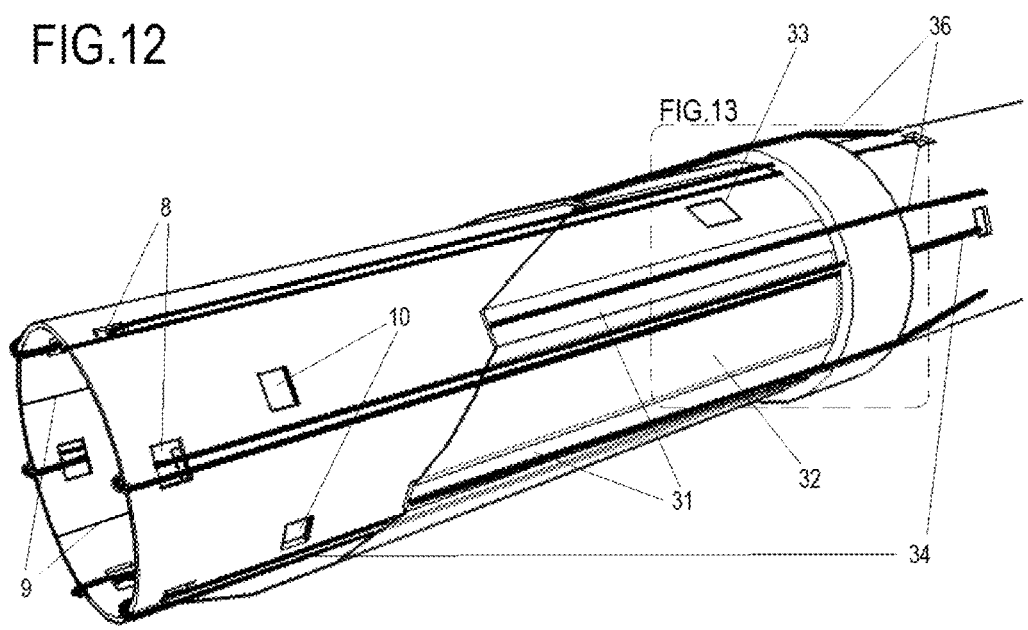
FIG. 12 shows the mold on the tip of the first embodiment in it un-deployed closed position before the trigger is pulled.

As shown in FIG. 12 prior to the pulling the trigger the mold rests on the outside tip of the embodiment. The deployment holes (8) are for a simple static pulley system to deploy the mold. The pull string (34) go from the cusp ring inside the housing, through the rear deployment holes, underneath the rigid guide members, through the deployment holes at the tip, and back to attach to the rigid guide members. Pulling these strings moves the rigid guide members forward. Attached to the guide members (31) are constraint strings (36) that have a constant length. When the constraint strings (36) become taught, the rigid guide members (31) are forced to lift away from the housing as the ring connecting the guide members moves forward. This change is highlighted by before (FIG. 12) and after (FIGS. 11A and 11B) views of the mold.

FIGS. 11A and 11B show the open mold of the first embodiment and the labeled sub-portions. When the trigger is pulled (45), elements move forward including the rotating cannula. In the cusp (23) of the rotating cannula is a ring (35) that is attached to the pull strings (34) that deploy the mold. The strings are looped through several holes in the housing (8) so that when the rotating cannula moves inside the housing the rigid guide members (31) move forward on the outside of the housing.

Figure 13:
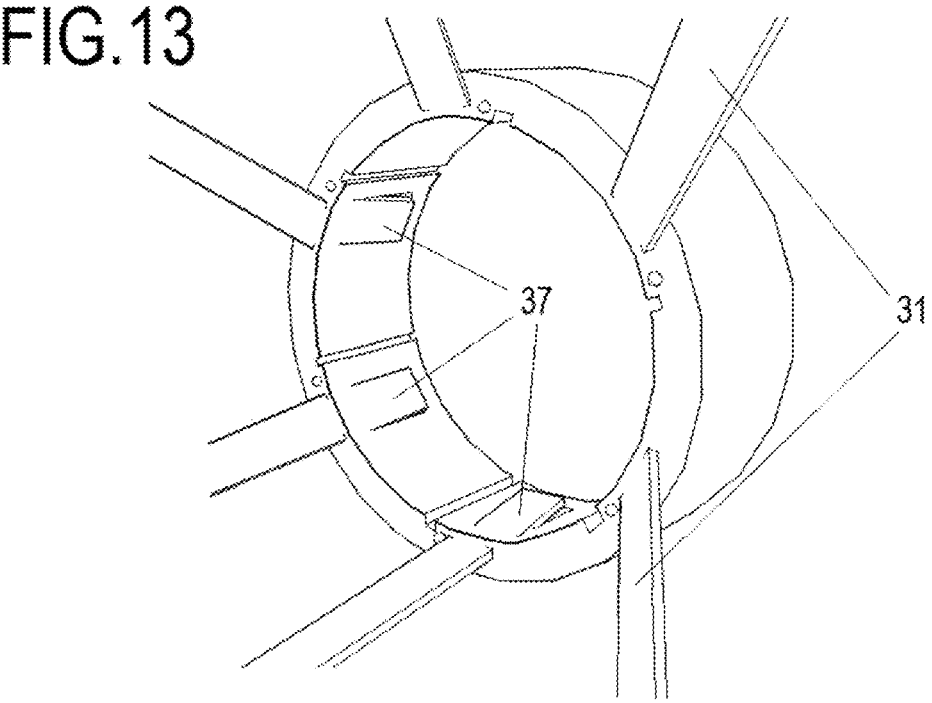
FIG. 13 shows the rigid guide members that are a sub-portion of the mold.

As shown in FIG. 13 the rigid guide members (31) are connected on a ring. The interior of the ring has six housing lock flanges (37) that lock into the mold lock holes (10) of the housing once the rigid guide members have moved to the tip of the housing. After this point the pull strings (34) will become slack as the rotating cannula moves back during rotation due to the dynamic threads. The rigid guide members (31) are attached and surrounded by an elastic sheet material mold (32) that opens when the rigid guide members move forward. The elastic mold is what contains the compound when it's injected. The rigid guide members facilitate its stretching and expansion to shape.

Figure 3:
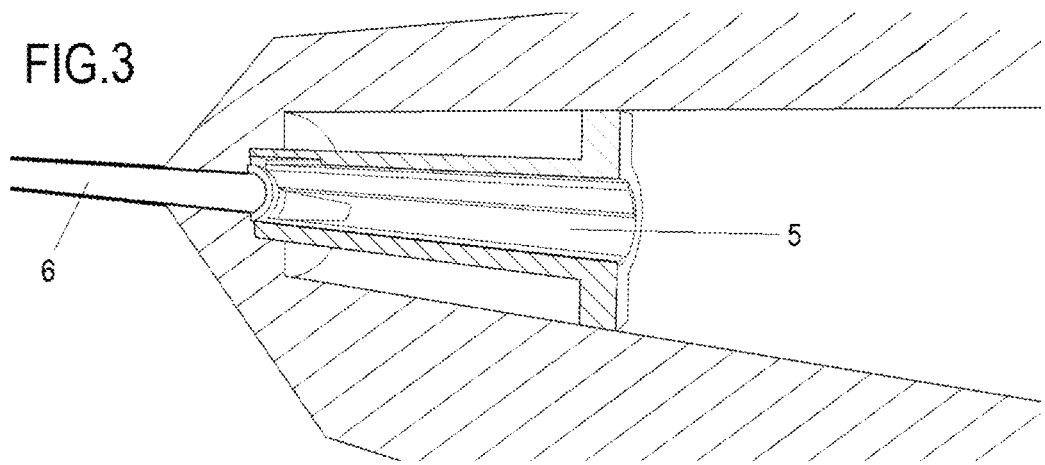
FIG. 3 shows the interior of the housing a section cut indicated in FIG. 2.

FIG. 3 shows the internal structure of the back-thread housing (5). The back-thread housing has three grooves for the three dynamic threads shown in FIG. 10 that move forward when the rotating cannula moves forward (45). The back-thread housing ends in a wider section so that the dynamic threads can expand and lock in place.

Figure 10:
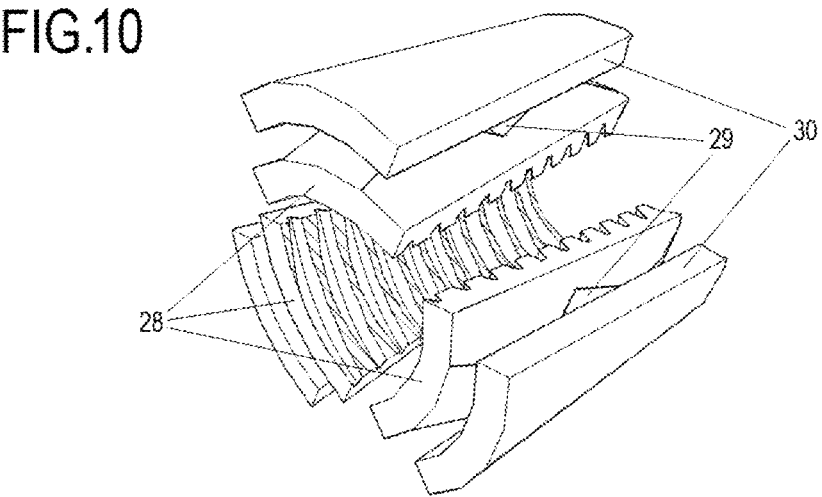
FIG. 10 shows the dynamic threads and the sub-portions of the first embodiment.
Figure 16:
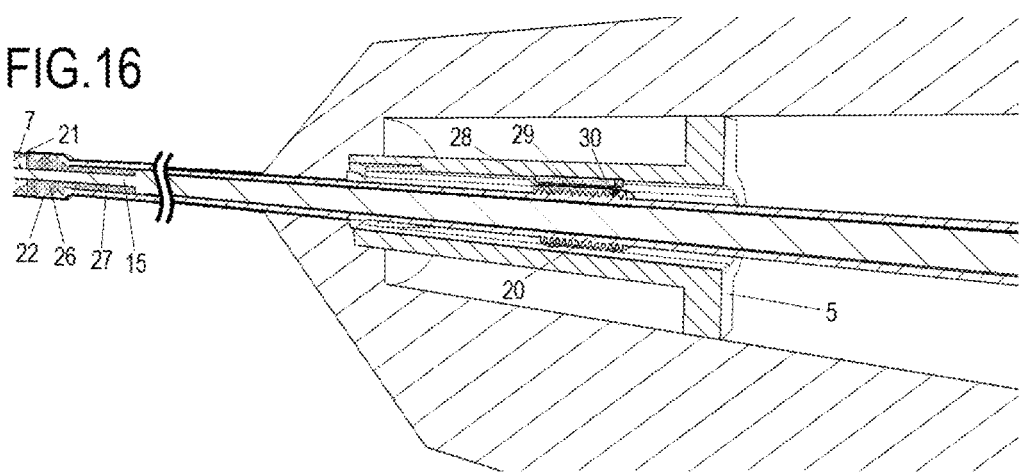
FIG. 16 shows a cross section of the assembled device.

As shown in FIG. 10 the dynamic threads of the first embodiment have three sub-portions and are replicated in triplicate. The dynamic threads go on the outside of the rotating cannula on the back-threads (20) as shown in FIG. 16. They are compressed inside the grooves of the back-thread housing (5). The arc spring (29) between the lock plate (30) and thread-plate (28) force the dynamic threads to expand. When the rotating cannula moves forward the dynamic threads move with it until the back thread housing (5) increases diameter allowing the dynamic threads to expand and the lock plate (30) opens into the space. This prevents the threads from being able to move back out of the grooves. The thread plate (28) is attached to the rotating cannula back-threads (20) and since the threads cannot move past each other the rotating cannula is also locked from retracting without rotation of the cannula.

When the trigger is pressed the central rod is locked from retracting by the position flange (3) holding the position groove (14) of the central rod. The rotating cannula is locked in place when the dynamic threads expand into the end of the back-thread housing. Thus after the trigger is pulled it cannot be reversed.

As shown in FIG. 18 the next step by the user is to fine tune the position of the deployed elements. Pulling the trigger simultaneously deployed both the mold and the insert. The insert should have flowered open into the defect so that the flexible disk material is in the hole but on the brain side of the skull base defect. The mold also deployed open and should be entirely on the sinus side of the defect and pressed firmly against the back of the sinuses so that when compound is injected it cannot migrate.

Figure 4:
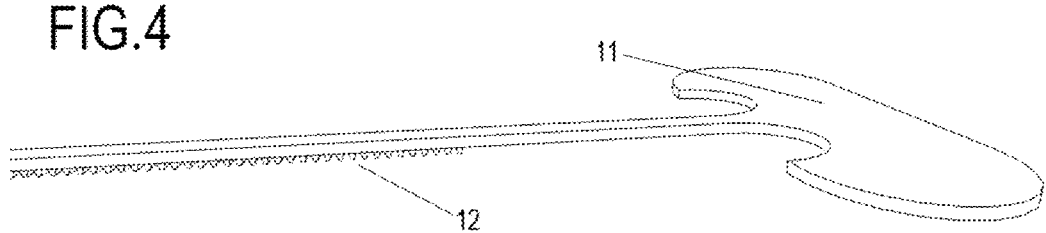
FIG. 4 shows the gear strip and the sub-portions of the first embodiment.

As shown in FIG. 4 the gear strip of the first embodiment has two sub-portions. These include the handle (12) where the user grips the gear strip to pull it and the strip (11) which pulls on the gear (19) of the rotating cannula. The length of the strip determines the number of rotations the rotating cannula will turn when the gear strip is pulled.

Figure 7B:
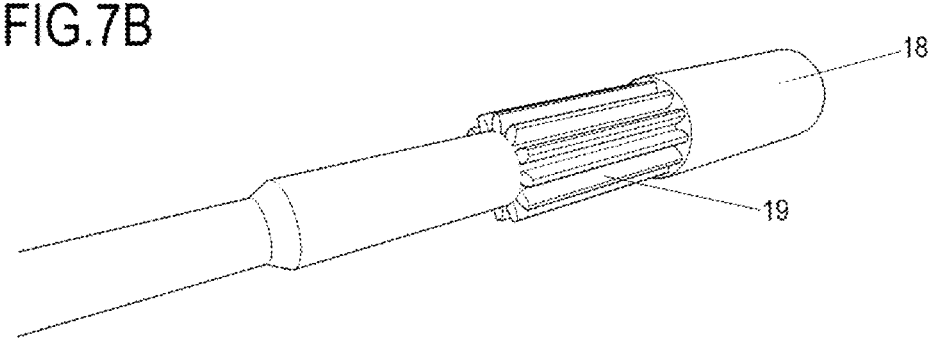
FIG. 7B shows a close up view of the end of the rotating cannula around the gear.
Figure 7C:
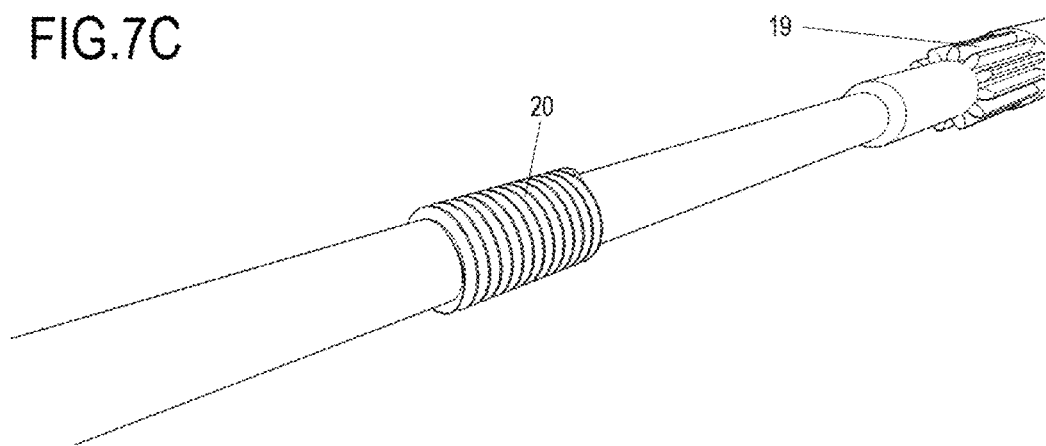
FIG. 7C shows a close up view of the mid-section of the rotating cannula around the back-threads.
Figure 7D:
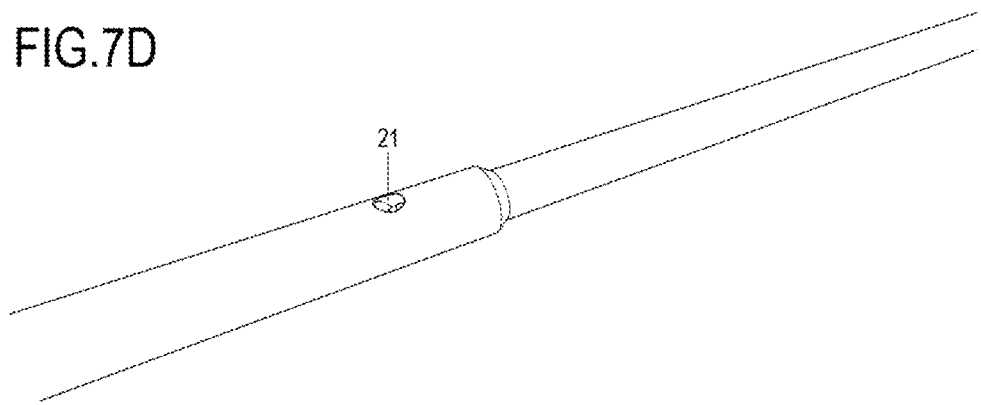
FIG. 7D shows a close up view of the front of the cannula around the initiation of the compound push threads omitting the tip shown clearly in FIG. 7A.

As shown in FIG. 2 there is a hole for the gear strip (4) that is just wide enough for the gear strip to enter. As shown in FIG. 7B the rotating cannula has a gear (19). This gear is wide so that as the cannula retracts, the thin gear strip (11) will meshes with it during its entire retraction. The gear strip pulls and rotates the cannula while the cannula slowly retracts. This action powers a multitude of simultaneous actions during the next step (47) of using the device.

As shown in FIG. 18 the next step is to pull the gear strip and inject compound. Compound has previously been injected into the tip of the device via the compound holes (7 & 21). After the trigger is pulled the cannula has moved forward thus the holes no longer line up. Compound can only leave the device through the tip of the cannula.

Figure 8A:
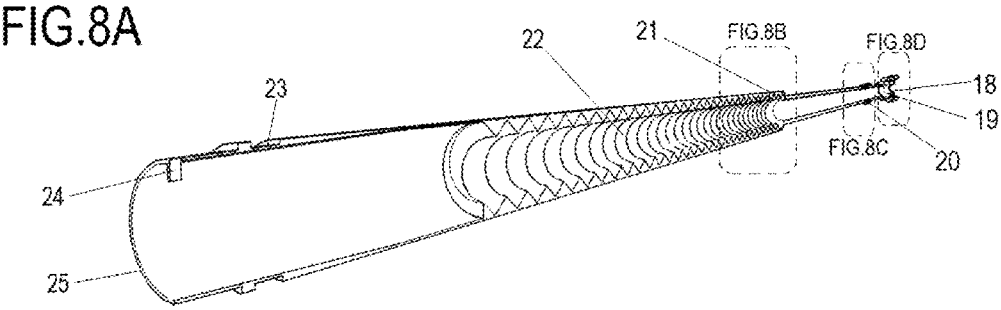
FIG. 8A shows a cross section of the rotating cannula down its midline to show the interior structures of the rotating cannula.
Figure 8B:
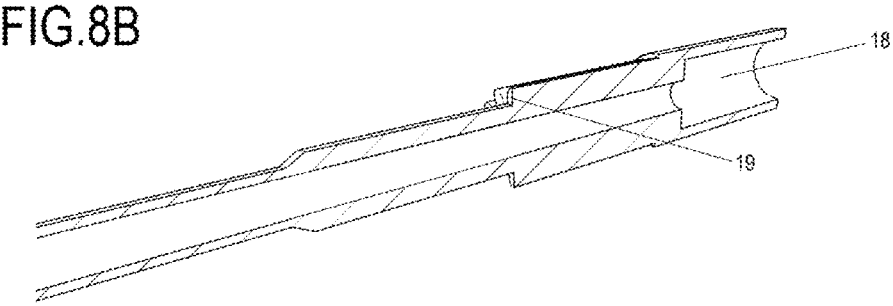
FIG. 8B shows a cross section of the rotating cannula with a close up view of the end of the cannula similar to FIG. 7B.
Figure 8C:
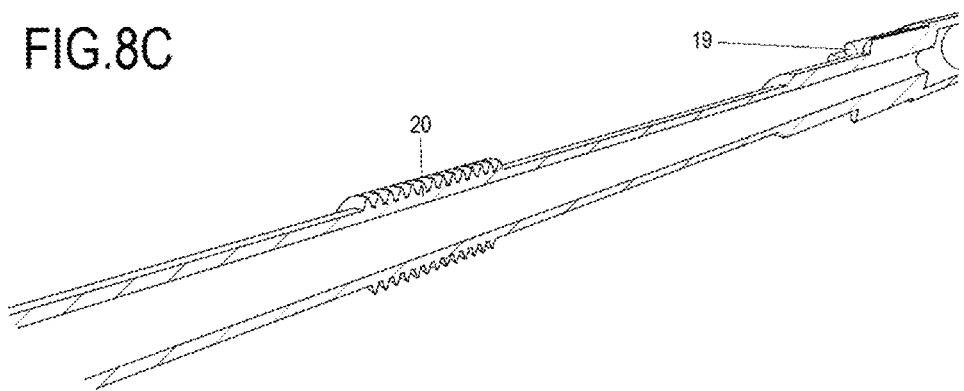
FIG. 8C shows a cross section of the rotating cannula with a close up view of the mid-section of the cannula similar to FIG. 7C.
Figure 8D:
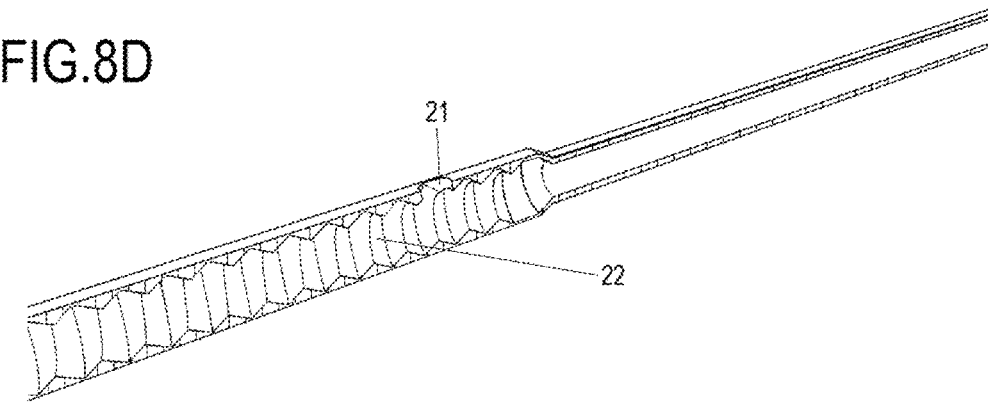
FIG. 8D shows a cross section of the rotating cannula with a close up view of the front of the cannula similar to FIG. 7D.
Figures 9A, 9B:
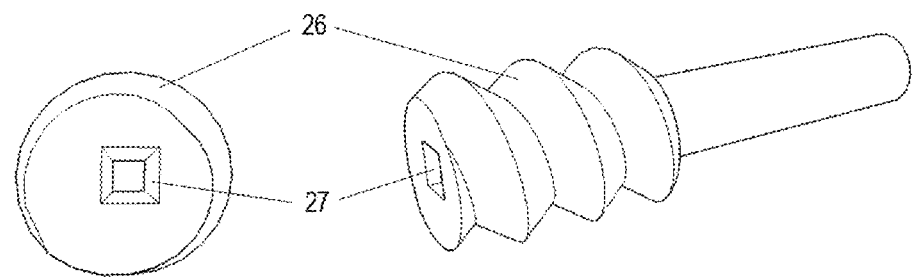
FIG. 9A shows a front view of the plunger and the sub-portions of the first embodiment.
FIG. 9B shows a side profile view of the plunger and the sub-portions of the first embodiment.

As shown in FIG. 8D the interior of the cannula is lined with course threading (22). As shown in FIG. 17 the plunger (26) is meshed with this threading (22). The squared guide hole of the plunger (27) keeps the plunger from rotating but it can still move down the length of the central rod (15). Thus when the gear strip is pulled (47), the cannula rotates around the plunger while the plunger is kept from rotating by the central rod. The plunger moves down the central rod pushing the compound that has previously been injected into the threaded cavity.

As shown in FIG. 16 the dynamic threads shown in detail in FIG. 10 are threaded onto the back-threads of the rotating cannula and are inside the back-thread housing (5). It is important to note that the compound threads (22) and the back-threads (20) are threaded in opposite directions. The back-threads are also at a much shallower angle than the compound threads. Thus with counter-clockwise rotation of the cannula, the plunger is pushed forward quickly while the whole cannula retracts slowly.

The cannula begins injecting compound into the skull base defect with the tip of the cannula nearly inside the skull base defect. This ensures penetration of compound to encase the interior and exterior of the edge of the skull base defect. Physically surrounding the edge of the defect with compound ensures that the physical strength of the cured compound not just its adhesive properties are responsible for maintaining a tight seal. The cannula retracts via the back-threads (20) so that there is not excessive injection of compound into the brain cavity. Retraction also ensures that compound is injected to surround and encase the constraint strings (40) of the insert. Once cured the compound around the constraint strings will hold the strings and attached flexible disk material firmly in place.

When the back-threads (20) have made enough rotations to thread off the dynamic threads the cannula stops retracting. The cannula is restricted from retracting further by the central rod guide shown in FIG. 8B. This collar ends in a reduction of diameter creating a face that corresponds to face 52 shown in FIG. 5. The cannula is sandwiched between the dynamic threads and the central rod which is still locked in position by its position groove (14) and lock flange (3). Although retraction has stopped at a set distance the gear strip continues to pull and strictly rotate the cannula.

At the same time as the back-threads are coming off the dynamic threads the plunger is pushing compound out the tip of the cannula. As shown in FIG. 5 the central rod has a squared guide (15) and a round guide (16). The compound threads stop pushing compound via the plunger when the plunger moves off the squared guide (15) onto the round guide (15) of the central rod. Since the round guide does not restrict the rotation of the plunger, when the plunger moves forward onto the round guide it rotates with the cannula and no longer pushes compound out of the cannula. The cannula continues to rotate after it has stopped pushing compound so that the leftover compound in the tip can be separated from the compound in the skull base seal before it cures and hardens.

As shown in FIG. 7A there is flange at the tip of the cannula called the compound scrapper (24). When the cannula has finished retracting the compound scraper (24) will be at the edge where the bonding protector (17) of the central rod buts up against the stalk (39). While compound has been injected out the tip of the cannula the bonding protector has prevented any of this compound from touching the end of the stalk. The compound scraper (24) is at the tip of the cannula (25) and when the gear stick is pulled it rotates around the edge of bonding protector (17) and stalk (39). This rotating action scrapes the edge of the central rod and stalk clean. This separates curing compound that has been injected into the mold from the leftover compound held up in the embodiment. Thus once the compound has cured and hardened the embodiment can still be removed from the nasal cavity leaving the seal in the skull base defect.

As shown in FIG. 18 after the compound has been injected the user must wait for the compound to cure and irrigate the plug with water. As shown in FIGS. 11A and 11B there is a hole in the mold (33). This allows direct contact between fluid and compound within the mold. This is important because many compounds that could be used with this embodiment release substantial heat when curing. If the compound is not cooled the rapid generation of heat could injure surrounding tissue. Thus there is a hole in the mold so that user can irrigate the insert so that heat can be absorbed by water and trafficked away from tissue while the compound is curing.

As shown in FIG. 18 after the compound has hardened and cured the seal must be separated from the embodiment that implanted it. At this stage the only connection between the seal and the embodiment is through the constraint strings (40) of the insert. Fortunately since the constraint strings are within the mold they have been surrounded and encased in hardened compound. As shown in FIG. 15B the constraint strings are attached to the tip of the housing by thread grooves (9). As stated previously the constraint strings (40) can be pulled from the grooves (9) with force in excess of that required to deploy the insert.

The position flange (3) holds the central rod from moving back but it can still move forward. After the compound has cured squeezing the trigger pushes the central rod forward which pushes on the compound stalk. Since the compound has cured the stalk cannot move forward, squeezing the trigger pushes the whole embodiment back off of the insert. At this point the constraint strings (40) pull out of the thread grooves (9) and all attachment between the insert and the rest of the embodiment is severed.

As shown in FIG. 18 the final step is to remove the embodiment from the patient's sinuses. Now that the seal has been separated from the embodiment, it can be removed from the patient leaving the insert/compound skull base seal in the patient.

As shown in FIG. 21 the seal left in the patient contains the elements of the insert and the cured compound injected (67). The flexible disk material (38) is on the sella turcica and held in place by the stalk (39) and the constraint strings (40) embedded in the cured compound (67). The cured compound wraps around the edges of the hole in the bony anatomy to ensure a secure water tight seal. Regardless of the embodiment used to insert the seal, the seal left in the patient will be in this general form but custom to the anatomy of each individual.

Figure 22:
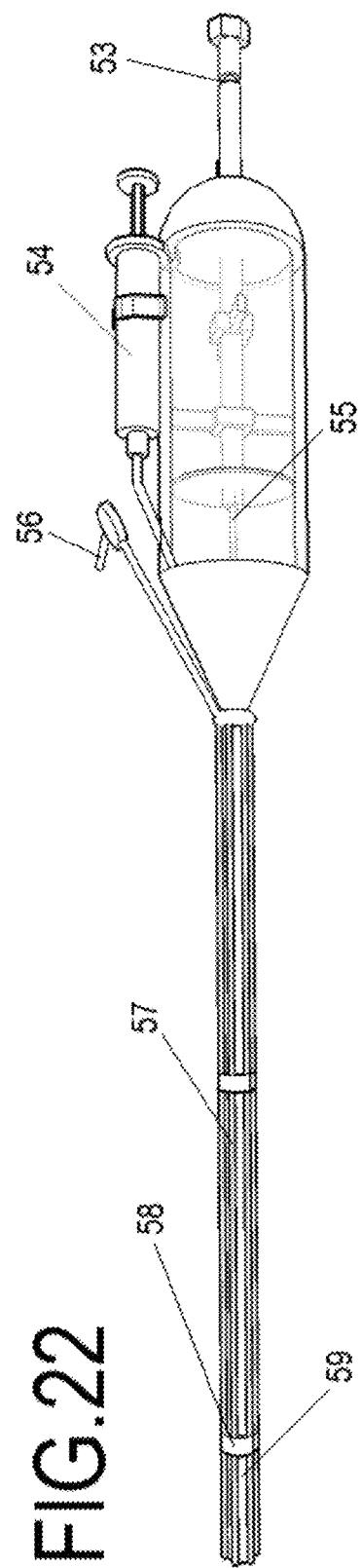
FIG. 22 shows a side profile of a second embodiment of the device.

As shown in FIG. 22 other embodiments exist to implant the seal in the patient. This embodiment uses a plunger (54) to push cement out the tip of the embodiment. The central rod (55) pushes the stalk of an insert similar to the first embodiment out of the tip but does not have any additional functions or interaction. There is a deployable mold (59) similar to that of the first embodiment but this one is attached to a suction apparatus (56,57,58). There are six tubes (57) running around the exterior of the cannula that connect to a suction rod (56). The suction rod can be connected to an external suction source. Connecting the tubes around the cannula are cuff rings (58).

Figure 26:
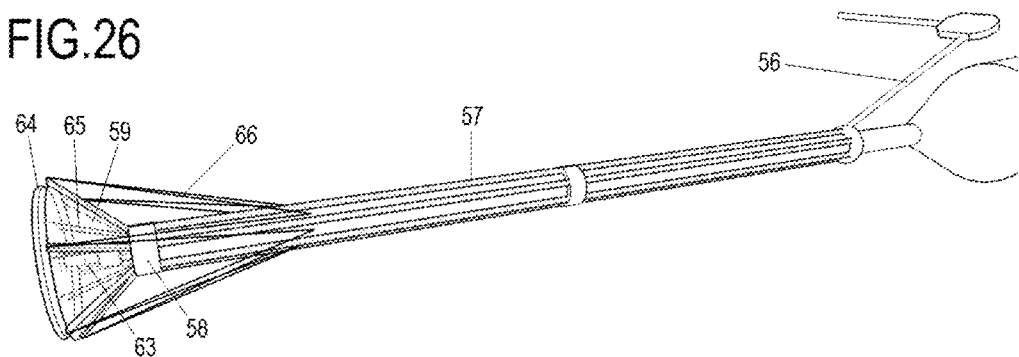
FIG. 26 shows the tip of the second embodiment of the device with the insert and suction apparatus deployed.

As shown in FIG. 26 the mold (59) is deployed when the suction rod moves forward. The suction tubes (57) move forward along the exterior of the cannula and the cuff rings (58) keep the suction tubes from bending so that they push the mold forward and open. After the last cuff ring the suction tubes are connected by a cylindrical sheet of elastic material that expands to make the mold. The suction tubes move forward and the constraint strings (66) cause them to lift away from the cannula to open the mold similar to the first embodiment. After the last cuff ring the suction tubes have a plurality of holes through the sides of the tubes. Thus any fluid flowing over the exterior of the mold will be sucked up by the tubes and pass out of the sinuses via suction attached to the suction rod.

Figure 23:
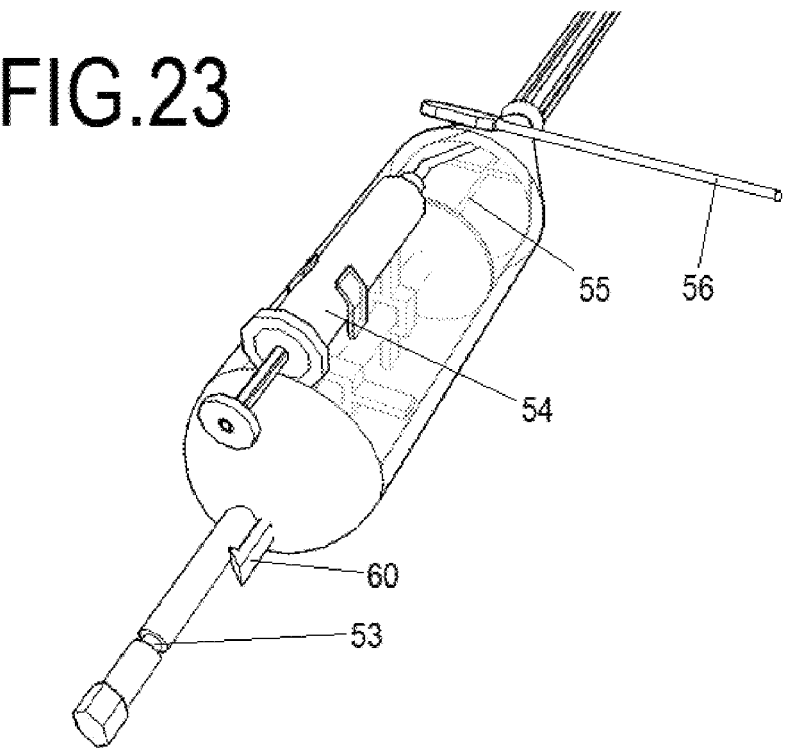
FIG. 23 shows a rear view of a second embodiment of the device.

As shown in FIG. 23 the second embodiment has a position flange (60) and a position groove (53) in the central rod similar to the first embodiment. Unlike the first embodiment there is no handle or trigger.

Figure 24:
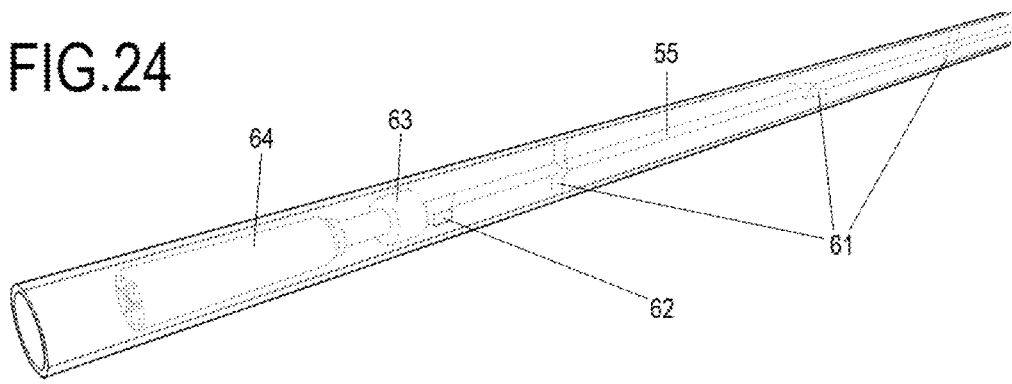
FIG. 24 shows the tip of the second embodiment of the device with the suction apparatus omitted.

As shown in FIG. 24 the insert made up of a flexible disk material (64) and a stalk (63) are mounted on the end of the central rod similar to the first embodiment. The central rod is thin thus there are several supports (61) within the cannula to support it and keep it positioned down the center of the cannula. There is a compound scrapper (62) on the end of the central rod to separate compound in the seal from the hold up of the device when it is rotated.

Figure 25:
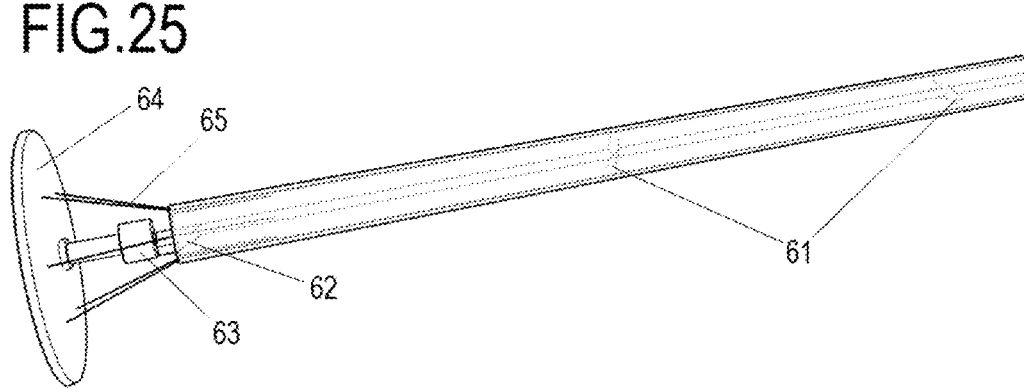
FIG. 25 shows the tip of the second embodiment of the device with the suction apparatus omitted and the insert deployed.

As shown in FIG. 25 when the central rod moves forward it deploys the insert. It does this by pushing the stalk (63) against the constraint strings (65), which pull the flexible disk material open. When the central rod moves forward the compound scrapper comes to the opening of the cannula so that it can separate curing compound inside and outside the cannula. Like with the first embodiment the curing of compound around the insert constraint strings (65) immobilizes them and allows the constraint strings to be pulled from grooves in the tip of the cannula when the central rod pushes forward. This embodiment would leave a seal in a patient similar to that produced by the first embodiment.

It will be recognized by one skilled in the art that other variations upon the described embodiment are possible within the teachings of the invention. For example, a detachable disposable tip that connects in the clamp site region could be used. Or, an electric motor could supply the rotating motion supplied by the gear strip of the first embodiment. Compound components could be contained in the tip of the embodiment and a way of mixing them as they pass out of the tip. Another embodiment could exchange compound push threads for a plunger to push compound out of the embodiment. The central rod could push directly on the flexible disk material to deploy the insert removing the stalk as an element of the insert. It is also possible to remove the insert from the device and use just compound in a mold to seal the defect.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. An injector for sealing a skull base defect in bony cranial anatomy, comprising:
   a) an elongated tubular cannula comprising:
      i) a body having a distal end and a proximal end, and a lumen extending axially from the distal end to the proximal end,
      ii) an expandable sheath on the distal end of the body comprising a plurality of rigid non-elastic material members connected by their proximal ends, with elastic material spanning the space between members, for creating a conical mold into which a compound can be injected;
      iii) a central member running through the lumen, being movable along a central axis of the lumen; and
   b) a plunger for pushing a compound through the lumen, such that operation of the plunger causes the compound to be injected from the distal end of the cannula into the conical mold formed by the expandable sheath.

2. The injector of claim 1, in which the plunger is within the lumen.

3. The injector of claim 1, in which the plunger is on the proximal end of the body.

4. The injector of claim 1, in which the compound is a formulation of bone cement.

5. The injector of claim 1, in which the central member comprises an end for holding an insert.

6. The injector of claim 1, further comprising a housing surrounding the cannula.

7. The injector of claim 6, in which the housing comprises a tip having a plurality of grooves for engaging constraint strings of an insert.

8. The injector of claim 1, in which the plunger and the central member further comprise intermeshing threads, such that rotation of the cannula causes the plunger to operate to inject the compound.

9. The injector of claim 8, further comprising a gear strip meshing with the threads on the central member, such that the rotation of the cannula to inject cement also causes retraction of the cannula.

10. The injector of claim 1, further comprising a trigger coupled to the central member, for moving the central member along the central axis of the lumen.

* * * * *